US006713620B2

(12) United States Patent
Padmanabha et al.

(10) Patent No.: US 6,713,620 B2
(45) Date of Patent: Mar. 30, 2004

(54) **OLIGONUCLEOTIDE PRIMERS FOR PHOSPHOTIDYL INOSITOL IN *BACILLUS CEREUS***

(75) Inventors: Padmapriya Banada Padmanabha, Mysore (IN); Ramesh Aiyagari, Mysore (IN); Chandrashekar Arun, Mysore (IN); Keshava Nireshwalia, Mysore (IN); Varadaraj Mandyam Chakravarathy, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/820,203

(22) Filed: Mar. 28, 2001

(65) Prior Publication Data

US 2003/0104373 A1 Jun. 5, 2003

(51) Int. Cl.$^7$ .......................... C12Q 1/68; C12P 19/34; C07H 21/02; C07H 21/04

(52) U.S. Cl. .................. 536/24.32; 536/24.3; 536/23.7; 536/24.33; 536/23.1; 435/6; 435/91.1; 435/91.2

(58) Field of Search .......................... 435/6, 91.1, 91.2; 536/23.7, 24.32, 23.1, 24.1, 24.33

(56) References Cited

PUBLICATIONS

Kuppe et al, Journal of Bacteriology, Nov. 1989, p. 6077–6083.*

GenBank Accession #M30809 *B. cereus* phosphat. BCT Apr. 26, 1993.*

GenBank Accession #G15398 Human Primer sequence, Jan. 4, 1996.*

Damgaard, P.H., et al. "Development and application of a primer set for specific detection of Bacillus . . . " *Systematic and Applied Microbiology*, vol. 19, No. 3 (1996) pp 436–441.

Kuppe, A.,et al. "Phosphatidylinositol–Specific Phospholipase C of *Bacillus–cereus*: Cloning, Sequencing . . . " *Journal of Bacteriooology*, vol. 171, No. 11 (1989) pp 6077–6083.

* cited by examiner

*Primary Examiner*—Carla J. Myers
*Assistant Examiner*—Sally Sakelaris
(74) *Attorney, Agent, or Firm*—Ladas & Parry

(57) ABSTRACT

The present invention provides novel oligonucleotide primers for phosphotidyl inositol in *B. cereus* the primer comprising

```
PI-1 (F) 5' AGTATGGGGAATGAG 3'
PI-1 (F) 5' ACAATTTTCCCACGA 3'
``` and to a method for the detection of *B. cereus* in foods in a mixed microflora.

3 Claims, No Drawings

SEQUENCE LISTING

```
<160> NUMBER OF SEQ ID NOS: 2

<210> SEQ ID NO 1
<211> LENGTH: 15
<212> TYPE: DNA
<213> ORGANISM: Bacillus cereus

<400> SEQUENCE: 1
agtatgggga atgag                                                    15

<210> SEQ ID NO 2
<211> LENGTH: 15
<212> TYPE: DNA
<213> ORGANISM: Bacillus cereus

<400> SEQUENCE: 2
acaattttcc cacga                                                    15
```

US 6,713,620 B2

OLIGONUCLEOTIDE PRIMERS FOR PHOSPHOTIDYL INOSITOL IN BACILLUS CEREUS

FIELD OF THE INVENTION

The present invention relates to a novel oligonucleotide primer for phosphoridyl inositol in *Bacillus cereus*. The present invention also relates to to a method for the detection of *Bacillus cereus* in food.

BACKGROUND OF THE INVENTION

Among the predominantly occurring food borne pathogenic bacteria, *Bacillus cereus*, an opportunistic pathogen has been found to occur abundantly in Indian foods and also cause illnesses like diarrhoea and/or emesis (Rakh et al. 1988). The illness has been attributed to the presence of enterotoxins and other toxins including haemolysins elaborated by strains of *B. cereus*. Conventionally, *B. cereus* is detected by its ability to grow on selective plating media containing egg yolk and inability to utilize mannitol. The isolates are further identified by morphological, cultural and biochemical characteristics. (Duguid, 1996).

Advances made in detection methods have led to the use of polymerase chain reaction (PCR) for the specific detection of *B. cereus*. PCR protocols have been developed for the detection of *B. cereus* group of bacteria in pure culture systems and food samples using specific sets of primers.

Reference is made to the work of Schrafts and Griffiths (1995), wherein primers for the cereolysin AB gene (M 24149) of *B. cereus* was designed. The detection limit for *B. cereus* by PCR in artificially contaminated milk samples was 103 CFU/ml without enrichment of the milk.

Reference is made to the works of Agata et. al. (1995) and Mantynen and Lindstrom (1998), wherein primers for the BceT gene was designed and used to study the distribution of the toxin gene in clinical and food isolates of *B. cereus*. Only qualitative observations were made on this work and no quantification has been reported. It was also postulated that the BceT gene could not be targeted to assess the enterotoxic potential of *B. cereus* strains.

Reference is made to the work of Wang et al. (1997), wherein a universal protocol for PCR detection of a number of food borne pathogenic bacteria was devised using haemolysin as the target gene. Detection of toxin producing strains of *B. cereus* was accomplished using these primers, following overnight enrichment of various food samples in a laboratory growth medium. This work provides only qualitative information and quantification was not addressed.

Reference is made to the work of Hsieh et al. (1999), wherein oligonucleotide primers were designed for sphingomyelinase gene and used for the PCR based detection of strains of *B. cereus* group in food samples. These primers can detect 100 cells/gram of the food sample only after an enrichment step for 8 hours indicating poor sensitivity Reference is made to the work of Yamada et al (1999) disclosing spiked boiled rice sample with varying cell concentrations of *B. cereus*. The rice sample was enriched in nutrient broth for different time intervals. No amplification was observed with non-enriched food samples with a gyrase D specific primers, even when the initial cell number was $10^4$ CFU of *B. cereus* per gram of boiled rice. Detection of low numbers of *B. cereus* by PCR was possible only after 15 hours enrichment in nutrient broth.

Reference is made to the work of Tsen et al. (2000), wherein primers were designed for 16s ribosomal RNA (Ribo Nucleic Acid) and used for PCR-based quantification of *B. cereus* spiked in food samples. Target cells ranging from 1 to 9 CFU/g of food sample could be detected only after 8 hours enrichment in brain heart infusion broth supplemented with glucose.

In German Patents DE 19915141 and DE 1991514 the sequences refer to 16s ribosomal RNA (Ribo Nucleic Acid) and gyrase B specific primers used for the detection of *Bacillus cereus*.

Reference is made to the work of Schrafts and Griffiths (1995) and Herman et al (1995), wherein a method for the isolation of target DNA from milk samples was devised. This method was elaborate comprising multitude of steps using combination of enzymes, detergents and column chromatography. The method also suffered from lack of sensitivity and could only detect $10^3$ CFU/ml. *B. cereus* by PCR using primers for cereolysin AB gene, Reference is made to the work of Yamada et al. (1999), wherein a protocol for the detection of *B. cereus* from boiled rice was described. The method included pre-enrichment step, two steps of filtration, followed by boiling of the samples prior to use in PCR. It was reported that at zero hour, a moderately high count of $2.4 \times 10^4$ CFU of *B. cereus* per gram of boiled rice failed to yield any PCR amplified product. Low numbers of *B. cereus* could only be detected after 15 hours of enrichment The drawback of all these methods have been non-specific detection of target organism i.e. *B. cereus*, lack of reproducibility, failure to detect all the isolates of *B. cereus* in a food system and lack of sensitiveness to detect low numbers of target organism. Besides, the methods are cumbersome and procedures are lengthy. The problem of formation of spores by *B. cereus* group of organisms makes detection by PCR a difficult proposition. In most of the methods a step of enrichment in a suitable laboratory growth medium is included which may take 8 to 15 hours of incubation for building up of cell numbers which can result in target DNA for use in PCR detection.

OBJECTS OF THE INVENTION

The main object of the present invention is to provide an improved method for the detection of *Bacillus cereus* in foods which obviates the drawbacks detailed above.

Another object of the present invention is to use a primer designed for a conserved region of a specific gene in the target organism.

Still another object of the present invention is to use the designed primer in detecting isolates which belong to *B. cereus* group.

Yet another object of the present invention is to detect *B. cereus* in food systems directly by PCR.

Still another object of the present invention is to use a simple and effective method for the preparation of template DNA (Deoxyribo Nucleic Acid) of the organism directly from the foods.

Yet another object of the present invention is to use PCR conditions specific for the detection of target gene in the organism.

Still another object of the present invention is to detect very low numbers of target organism in the food systems.

SUMMARY OF THE INVENTION

Accordingly, the present invention provides a novel oligonucleotide primer for phosphotidyl inositol in *B. cereus* said printer comprising

PI-1 (F) 5' AGTATGGGGAATGAG 3'    (SEQ ID NO: 1)

PI-1 (F) 5' ACAATTTTCCCACGA 3'    (SEQ ID NO: 2)

The present invention also refers to method for the detection of B. cereus in foods said method comprising using primers specific for phosphotidyl inositol gene in B. cereus in a mixed microflora, said primers comprising

PI-1 (F) 5' AGTATGGGGAATGAG 3'    (SEQ ID NO: 1)

PI-1 (F) 5' ACAATTTTCCCACGA 3'    (SEQ ID NO: 2)

In one embodiment of the invention, the food matrices for detecting B. cereus in milk and cooked rice.

In another embodiment of the invention, template DNA from B. cereus in cooked rice is extracted using Triton X-100, 0.5–2%, boiling at 96–100° C. for 3–8 min and treatment with phenol : chloroform in the ratio of 22:21–28.27.

In another embodiment of the invention, the template DNA from *B. cereus* in milk is extracted using diethyl ether:chloroform in the ratio of 1:1–1:3, urea 1.5 3.5 M and sodium dodecyl sulphate in a range of 0.5–2%.

In a further embodiment of the invention, the PCR reaction mixture in a total volume of 25 $\mu$l comprises of Tris HCl: 8–12 mM; KCl 45–55 mM, $MgCl_2$: 0.5–3.0 mM; gelatin: 0.005 0.02%; individual deoxynucleoside triphosphates: 150–300 $\mu$M; each specific primer: 30 60 picomoles; Taq DNA polymerase: 0.5–2.0) units and template DNA: 1–3 $\mu$l.

In another embodiment of the invention, detection of *B. cereus* is effected by amplification profile of target gene from an initial denaturation at 90–98° C. for 2–8 min, amplification cycles of 28–40, each cycle with a denaturation at 90–98° C. for 40–70 seconds, annealing at 46–54° C. for 40–80 seconds and an extension at 68–76° C. for 45–75 seconds and final extension at 68–76° C. for 4–12 min In another embodiment of the invention, analysis of the PCR product is done in 1.2–1.8% agarose gel electrophoresis, visualization of the PCR product by staining with 0.5 (g/ml ethidium bromide and observation in a UV transilluminator.

In yet another embodiment of the invention, detection of minimum number of cells of *B. cereus* is done in a food matrix by PCR.

DETAILED DESCRIPTION OF THE INVENTION

The present invention relates to an improved PCR method for the detection of *B. cereus* in foods. The PCR method using the primers of the invention detects 1 to 106 cells of *B. cereus* directly in foods. Polymerase chain reaction method is used to selectively amplify phosphotidyl inositol gene in *B. cereus*. Milk and cooked rice samples were spiked with varying cell numbers of *B. cereus* ranging from 1 to 1,000,000. Protocols for extraction of template DNA from *B. cereus* present in food matrix were standardized using detergents and organic solvents. The PCR reaction mixture and amplification conditions were optimized for the specific amplification. Visualization of PCR products revealed that by the method followed, it is possible to detect cell numbers ranging from 1 to 1,000,000 in milk and cooked rice samples.

The primers of the invention directly detect *Bacillus cereus* in food systems by PCR. This method can detect all the strains of *B. cereus*. The method is rapid and sensitive making it possible to detect even 1 cell in a food matrix overcoming any steps of enrichment.

The following examples are given by way of illustrations of the present invention and therefore should not be construed to limit the scope if the present invention.

EXAMPLE-1

Oligonucleotide primers for phosphotidyl inositol gene of *B. cereus* were designated based on the gene sequence (M 30809) using the software programme Primer 3.0. This primer set amplifies a 342 base pair (bp) fragment of the gene, the sequence of which is given below. Sterilization of media and other solutions was achieved by autoclaving for 20 mm at 121° C.

```
PI-1 (F) 5' AGTATGGGGAATGAG 3'    (SEQ ID NO: 1)

PI-1 (F) 5' ACAATTTTCCCACGA 3'    (SEQ ID NO: 2)
```

Aliquots in 100 $\mu$l of a native food isolate of *B. cereus* was inoculated into sterile 10 ml brain heart infusion (BHI) broth and incubated for 18 h at 37° C. in a shaker incubator with 140 rpm. Cells were harvested by centrifugation at 10,000 rpm for 10 min at 4° C. The cells were suspended in 10 ml sterile 0.85% saline to get a cell concentration of $10^9$ colony forming units per milliliter (CFU/ml). From this stock, serial dilutions in 9 ml sterile 0.85% saline were carried out to achieve cell concentrations ranging from $10^8$ to $10^1$ CFU/ml. The individual dilutions were used for spiking into milk samples.

Twenty milliliters of pasteurized milk was taken in a sterile screw capped tube of 25×125 mm dimension, steamed for 30 min in a cooker without any pressure and cooled to 30° C. In individual 1.5 ml sterile microcentrifuge tube, 0.4 ml of the cooled milk sample was mixed with 0.4 ml of 0.85% sale suspension of *B. cereus* to attain a final cell concentration ranging from of $10^6$, $10^5$, $10^4$, $10^3$, $10^2$, $10^1$ and $10^0$ CFU/ml. To each tube was added 0.25 ml each of diethyl ether and chloroform were added to the samples and vortexed for 30 seconds. The samples were centrifuged at 10,000 rpm for 15 min at 25° C. The aqueous phase was transferred to a fresh 1.5 ml sterile microcentrifuge tube and 0.5 ml of 6M urea and 0.1 ml of 10% sodium dodecyl sulphate were added. The samples were incubated at 37° C. for 20 min and then centrifuged 10,000 rpm for 15 min at 25° C. The supernatant was discarded and 0.1 ml of 0.2N NaOH was added to the samples and incubated at 37° C. for 10 min. DNA was precipitated by adding 1.0 ml of chilled absolute ethanol and 0.1 ml of 3M sodium aectate (pH 4.8) and holding the samples at −20° C. for 2 h. Samples were centrifuged at 10,000 rpm for 15 min at 4° C. The supernatant was discarded and excess salt in the DNA preparation was removed by adding 1.0 ml of chilled 70% ethanol and centrifuging the samples at 10,000 rpm for 15 min at 4° C. The supernatant was discarded and the DNA pellet was air-dried and resuspended in 15 (1 of sterile ultrafiltered water.

Amplification was performed in a total reaction volume of 25 $\mu$l which contained 2 $\mu$l of the DNA preparation from milk samples. The reaction mixture consisted of 1× PCR buffer (10 mM Tris HCl, pH 9.0, 50 mM KCl, 1.5 mM $MgCl_2$, 0.01% gelatin), 200 $\mu$M of each deoxynucleoside triphosphate, 50 picomoles of each primer and 1.0 unit of Taq DNA polymerase Template DNAs were initially denatured at 94° C. for 5 min. Subsequently, a total of 35 amplification cycles were carried out in a programmable thermocycler. Each cycle consisted of denaturation for 1 min at 94° C., primer annealing for 1 min at 50° C. and extension for 1 min at 72° C. The last cycle was followed by a final exension at 72° C. for 8 min.

PCR products were analysed by agarose gel electrophoresis. Aliquots of 10 µl PCR products were mixed with 2.0 µl of loading dye and loaded onto 1.5% agarose gel and subjected to electrophoresis for 2 h at 120 volts in 1× TAE buffer. Gel was stained with ethidium bromide (0.5 µg/ml), de-stained with distilled water and examined on a UV transilluminator. A 100 bp ladder was used as molecular size marker. The amplification profile in the gel was documented in a CCD-camera based Gel Documentation System.

The specific amplicons of 342 bp for phosphotidyl inositol were observed when PCR was performed with milk samples containing B. cereus cells ranging from 1 to 1,000,000.

EXAMPLE-II

Oligonucleotide primers for phosphotidyl inositol gene of B. cereus were designated based on the gene sequence (M 30809) using the software programme Primer 3.0. This primer set amplifies a 342 base pair (bp) fragment of the gene, the sequence of which is given below. Sterilization of media and other solutions was achieved by autoclaving for 20 mm at 121° C.

```
PI-1 (F) 5' AGTATGGGGAATGAG 3'    (SEQ ID NO: 1)

PI-1 (F) 5' ACAATTTTCCCACGA 3'    (SEQ ID NO: 2)
```

Aliquots in 100 µl of a native food isolate of B. cereus was inoculated into sterile 10 ml brain heart infusion (BHI) broth and incubated for 18 h at 37° C. in a shaker incubator with 140 rpm. Cells were harvested by centrifugation at 10,000 rpm for 10 min at 4° C. The cells were suspended in 10 ml sterile 0.85% saline to get a cell concentration of $10^9$ colony forming units per milliliter (CFU/ml). From this stock, serial dilutions in 9 ml sterile 0.85% saline were carried out to achieve cell concentrations ranging from $10^8$ to $10^3$ CFU/ml. The individual dilutions were used for spiking into cooked rice samples.

Raw rice in 1000 g quantity was taken, cleaned and washed with running tap water. Cleaned rice was mixed with water in 1:2 proportion, taken in a stainless steel container and steam cooked in a pressure cooker for 20 min. Cooked rice in 100 g aliquots were taken in individual sterile 500 ml glass beakers and was spiked with 1.0 ml saline suspension of B. cereus to get a cell concentration of $10^7$ CFU/g and mixed uniformly.

Spiked cooked rice samples in 11 g aliquots was then added to 99 ml sterile 0.85% saline taken in a 250 ml conical flask, mixed well and serial dilutions were prepared in sterile 0.85% saline to get individual cell concentrations of $10^6$, $10^5$, $10^4$, $10^3$, $10^2$, $10^1$ and $10^0$ CFU/g. Aliquots of 1 ml of diluted samples were transferred to a 1.5 ml sterile microcentrifuge tubes. The samples were centrifuged at 10,000 rpm for 5 min at 4° C. The pellet was washed thrice with 1.0 ml phospate buffered saline of pH 7.4 and once with 1.0 ml sterile ultrafilter water by centrifugation at 10,000 rpm for 5 min at 4° C. and discarding the washes. The pellet was resuspended in a mixture containing 50 µl sterile ultrafilter water and 450 µl sterile 1% Triton X-100. The samples were incubated in boiling water for 5 min 0.5 ml phenol:chloroform (25:24) was added to the sample, vortexed briefly and centrifuged at 10,000 rpm for 15 min at 4° C. The aqueous phase was transferred to a fresh 1.5 ml sterile microcentrifuge tube and 0.5 ml chloroform was added to the sample. The samples were centrifuged at 10,000 rpm for 15 min at 4° C. and the aqueous phase was transferred to a fresh 1.5 ml sterile microcentrifuge tube. DNA was precipitated by adding 1.0 ml chilled absolute ethanol and 0.1 ml of 3M sodium acetate (pH 4.8) and incubating the samples at −20° C. for 2 h. The samples were centrifuged at 10,000 rpm for 15 min at 4° C. Excess salt in the DNA pellet was removed by adding 1.0 ml chilled 70% ethanol and centrifuging the samples at 10,000 rpm for 15 min at 4° C. The supernatant was discarded. The DNA pellet was air dried and dissolved in 15 µl of sterile ultrafilter water.

Amplification was performed in a total reaction volume of 25 µl containing 2 µl of the DNA preparation from milk samples. The reaction mixture consisted of 1× PCR buffer (10 mM Tris HCl, pH 9.0, 50 mM KCl, 1.5 mM $MgCl_2$, 0.01% gelatin), 200 µM of each deoxynucleoside triphosphate, 50 picomoles of each primer and 1.0 unit of Taq DNA polymerase. Template DNAs were initially denatured at 94° C. for 5 min. Subsequently, a total of 35 amplification cycles were carried out in a programmable thermocycler. Each cycle consisted of denaturation for 1 min at 94° C., primer annealing for 1 min at 50° C. and extension for 1 min at 72° C. The last cycle was followed by a final extension at 72° C. for 8 min.

PCR products were analysed by agarose gel electrophoresis. Aliquots of 10 µl PCR products were mixed with 2.0 µl of loading dye and loaded onto 1.5% agarose gel and subjected to electrophoresis for 2 h at 120 volts in 1× TAE buffer. Gel was stained with ethidium bromide (0.5 (g/ml), destained with distilled water and examined on a UV transilluminator. A 100 bp ladder was used as molecular size marker. The amplification profile in the gel was documented in a CCD-camera based Gel Documentation System.

The specific amplicons of 342 bp for phosphotidyl inositol were observed when PCR was performed with cooled rice samples containing B. cereus cells ranging from 1 to 1,000,000.

The main advantages of the present invention are:

1. The designed phosphotidyl inositol primers is specific for the detection of B. cereus.
2. In a mixed microflora, the designed primer set specifically detects B. cereus with no cross reactivity.
3. A simple and effective protocol for extraction of template DNA for B. cereus present in a varied food matrix.
4. Standardized PCR conditions for the detection of B. cereus present in milk and cooked rice.
5. A rapid and sensitive PCR method which can detect even 1 cell of B. cereus in food system.

We claim:

1. A novel set of nucleotide primers for phosphotidyl inositol in *B.cereus*, said set of primers comprising:

PI-1(F) 5' AGTATGGGGAATGAG 3' (SEQ ID NO: 1)

and

PI-1(F) 5' ACAATTTTCCCACGA 3' (SEQ ID NO: 2).

2. The novel set of oligonucleotide primers according to claim 1, said set of primers consisting of:

PI-1(F) 5' AGTATGGGGAATGAG 3' (SEQ ID NO: 1)

-continued and

PI-1(F) 5' ACAATTTTCCCACGA 3' (SEQ ID NO: 2).

3. The novel set of oligonucleotide primers according to claim 1, said set of primers consisting essentially of:

PI-1(F) 5' AGTATGGGGAATGAG 3' (SEQ ID NO: 1)

and

PI-1(F) 5' ACAATTTTCCCACGA 3' (SEQ ID NO: 2).

* * * * *